United States Patent
Bingley et al.

(10) Patent No.: US 9,591,143 B2
(45) Date of Patent: Mar. 7, 2017

(54) MOBILE COMMUNICATION DEVICE CONNECTABLE TO A VITAL SIGN MONITORING SYSTEM

(71) Applicant: KONINKLIJKE PHILIPS N.V., Eindhoven (NL)

(72) Inventors: Peter Bingley, Mierlo (NL); Marius Leendert Trouwborst, Den Bosch (NL); Paul Augustinus Peter Kaufholz, Eindhoven (NL); Angelique Carin Johanna Maria Brosens-Kessels, Eindhoven (NL); Jia Du, Waalre (NL); Emmy Van Roosmalen, Eindhoven (NL); Marjolein Wilhelmina Maria Schets, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/736,600

(22) Filed: Jun. 11, 2015

(65) Prior Publication Data

US 2016/0021258 A1  Jan. 21, 2016

(30) Foreign Application Priority Data

Jun. 11, 2014 (EP) .................................. 14171903

(51) Int. Cl.
*A61B 5/00* (2006.01)
*H04M 11/04* (2006.01)
(Continued)

(52) U.S. Cl.
CPC ........... *H04M 11/04* (2013.01); *A61B 5/7465* (2013.01); *G06F 19/322* (2013.01);
(Continued)

(58) Field of Classification Search
CPC .................................................. A61B 5/0002
See application file for complete search history.

(56) References Cited

U.S. PATENT DOCUMENTS

2006/0003812 A1* 1/2006 Moody ..................... G08B 6/00
455/567
2007/0096897 A1* 5/2007 Weiner ................. A61B 5/0006
340/539.13
(Continued)

FOREIGN PATENT DOCUMENTS

WO   2008016535 A2   2/2008

*Primary Examiner* — Christopher M Brandt

(57) ABSTRACT

In one aspect, it is aimed to provide a mobile communication device that is connected to a communication module of a vital sign monitoring system in an intensive care unit, comprising:
a communication function responsive to vital sign indications of specified nature and origin of respective patients of the intensive care unit, produced by the vital sign monitoring system; wherein the application module is arranged to select a communication urgency level for the another designated professional based on a vital sign indication;
a user interface item for initiating communication with another communication device connectable to the vital sign monitoring system, wherein the user interface item is arranged to select another communication device of a further designated professional based on a received availability level of the designated person; and
a user interface item for accepting communication with another communication device seeking contact, said user interface item for accepting communication comprising an indicator of the selected urgency level based on the vital sign indication.

18 Claims, 4 Drawing Sheets

(51) Int. Cl.
*G08B 21/04* (2006.01)
*G06F 19/00* (2011.01)
*G08B 25/08* (2006.01)

(52) U.S. Cl.
CPC ..... *G06F 19/3425* (2013.01); *G08B 21/0415* (2013.01); *G08B 21/0476* (2013.01); *G08B 21/0492* (2013.01); *G08B 25/08* (2013.01); *G06F 19/327* (2013.01); *G06F 19/3418* (2013.01)

(56) References Cited

U.S. PATENT DOCUMENTS

| | | | |
|---|---|---|---|
| 2007/0155402 A1* | 7/2007 | Van Erlach | G06Q 30/0207 455/456.1 |
| 2007/0180036 A1 | 8/2007 | Hebert et al. | |
| 2009/0150441 A1 | 6/2009 | Johnsen et al. | |
| 2010/0305412 A1* | 12/2010 | Darrah | A61B 5/0002 600/301 |
| 2012/0029314 A1* | 2/2012 | Paquet | A61B 5/02055 600/301 |
| 2012/0197196 A1* | 8/2012 | Halbert | A61M 5/142 604/151 |
| 2012/0278104 A1* | 11/2012 | Traughber | G08B 5/222 705/3 |
| 2012/0310103 A1 | 12/2012 | Musiol et al. | |
| 2013/0024382 A1* | 1/2013 | Dala | G06F 19/322 705/51 |
| 2013/0054467 A1 | 2/2013 | Dala et al. | |
| 2014/0039912 A1* | 2/2014 | Turinas | G06F 19/322 705/2 |
| 2014/0248858 A1 | 9/2014 | Soomro | |
| 2015/0116112 A1 | 4/2015 | Flinsenberg et al. | |

* cited by examiner

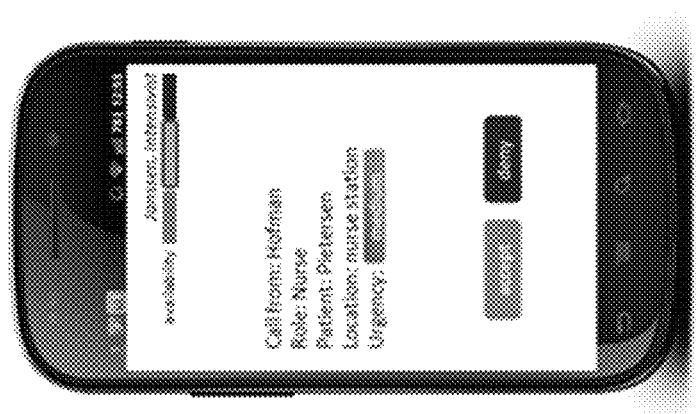
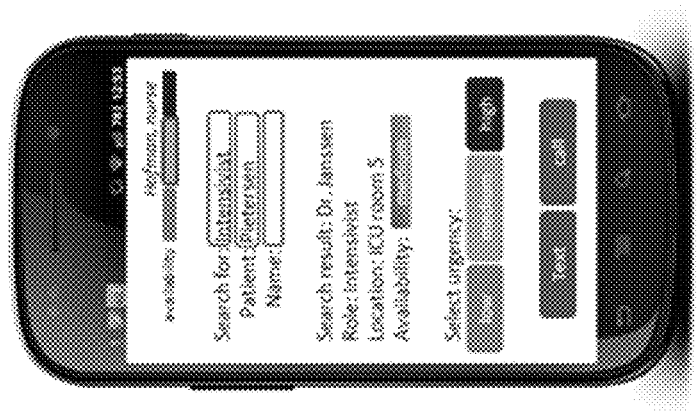
FIG 3

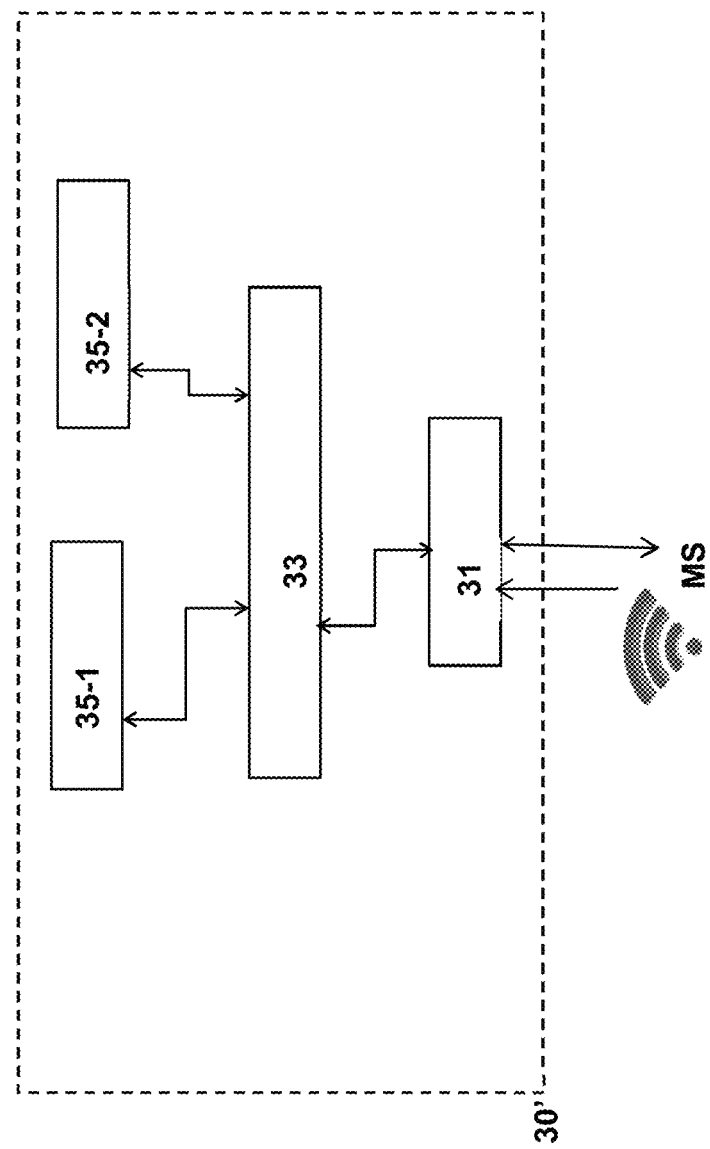

MOBILE COMMUNICATION DEVICE CONNECTABLE TO A VITAL SIGN MONITORING SYSTEM

FIELD OF INVENTION

The invention relates to a mobile communication device that is connectable to a vital sign monitoring system for use in hospitals; in particular in intensive care units. The invention also relates to a method of connecting a mobile communication device to a vital monitoring system and a computer program product for putting into effect the method.

DESCRIPTION OF THE PRIOR ART

The high number of interruptions in intensive care units can strongly disturb the work of the involved professional staff. For example, in practice, incoming phone calls are always answered immediately for they could be highly important messages. This can hinder the workflow, especially when the receiving party is busy with other important activities and when the message of the phone call has low importance.

Some solutions exist to forward medical data to other person's mobile devices, such as a smartphone, to actively assess medical data of a patient, such as vital signs on a mobile. For example US20130024382 discloses a messaging server that is used for communication of patient medical data in order to have these evaluated. However, this application is not related to the problem of contacting various professionals in a challenging environment.

SUMMARY OF THE INVENTION

In one aspect, it is aimed to provide a mobile communication device that is connectable to a communication module of a vital sign monitoring system in an intensive care unit comprising:

a communication function responsive to vital sign indications of specified nature and origin of respective patients of the intensive care unit, produced by the vital sign monitoring system; wherein the application module is arranged to select a communication urgency level for another designated professional based on a vital sign indication;

a first user interface item for initiating communication with another communication device connectable to the vital sign monitoring system, wherein the user interface item is arranged to select another communication device of a designated professional based on a received availability level of the designated person; and a second user interface item for accepting communication with another communication device seeking contact, said user interface item for accepting communication comprising an indicator of the selected urgency level based on the vital sign indication.

In a communication device as presently disclosed, a receiver using the mobile device, being a phone call, pager notification or text message may know how urgent the interruption is. In addition, the initiator of the communication is informed of the availability of the receiving party for his or her message so that disturbances are reduced for the activities of initiator and receiver.

BRIEF DESCRIPTION OF THE DRAWINGS

The invention will be further elucidated in the figures:

FIG. 3 shows an arrangement of mobile communication devices according to an embodiment;

FIG. 4 shows in more detail the arrangement of the mobile communication devices in FIG. 3.

DETAILED DESCRIPTION

Figure 1:
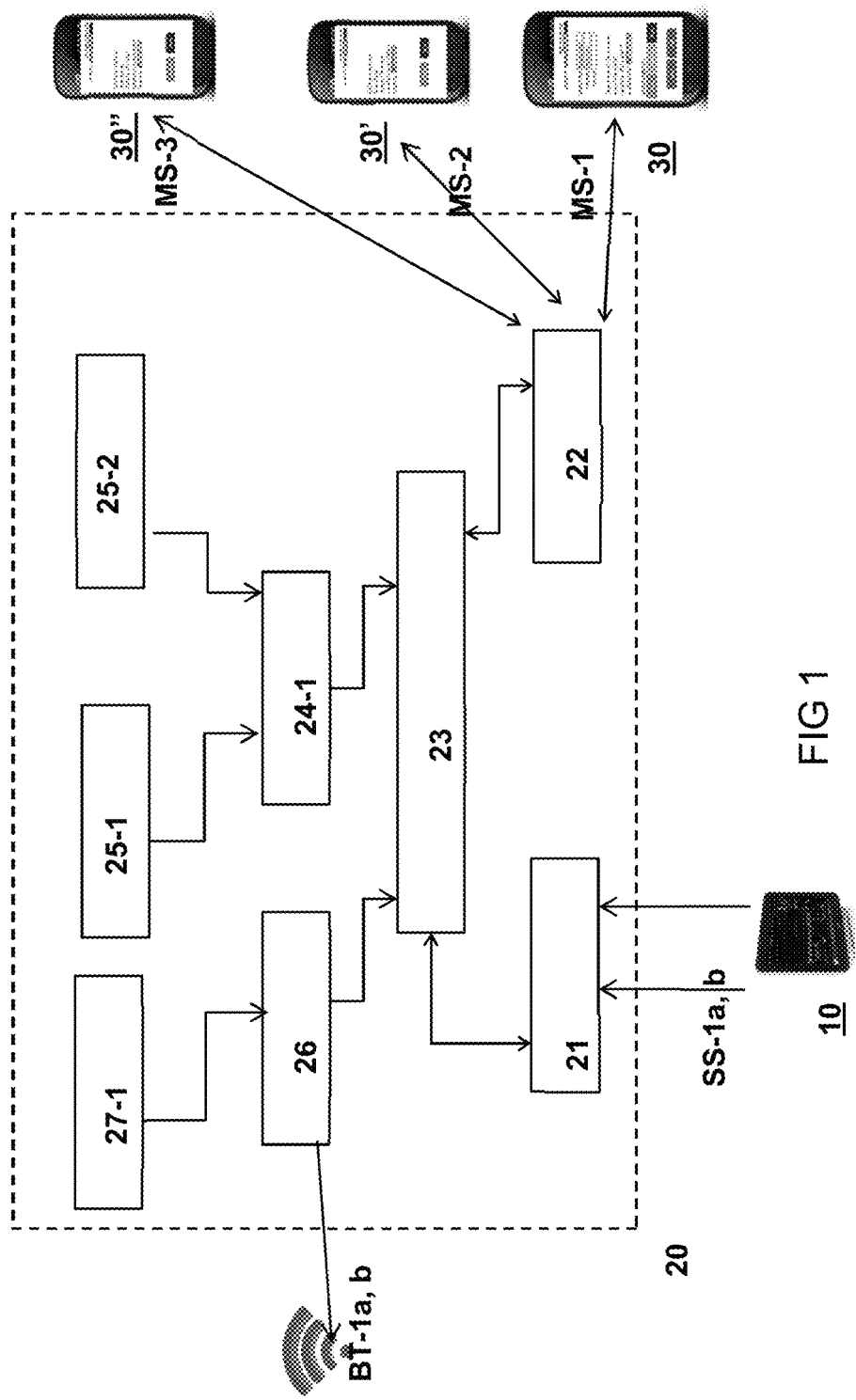
FIG. 1 shows a first embodiment of a vital sign monitoring system comprising plural mobile communication devices.

Unless otherwise defined, all terms (including technical and scientific terms) used herein have the same meaning as commonly understood by one of ordinary skill in the art to which this disclosure belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

The term "module" as in "application module", "activity monitor module" and "user module" is used to emphasize the modular character of these units, i.e. the functionality of the system is separated into independent, interchangeable units. A "communication function" may correspond to a unit capable of communicating with the vital sign monitoring system, and being responsive to vital sign communications of specified nature and origin respective to the vital sign detectors, produced by the vital sign monitoring system.

The term "user interface item", e.g. the "user interface control item" may comprise one or more hardwire elements configured to perform operational acts in accordance with the present systems and methods, such as to provide control signals to the various other module components. The processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include micro-controllers, central processing units (CPUs), digital signal processor s (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

FIG. 1 shows a schematic detailed constitution of a vital sign monitoring system 20. The system can be used in general departments of a hospital, provided with vital sign monitoring functionality in particular, heart beat, respiratory, temperature and/or oxygen saturation detection functions. The system is especially useful for intensive care units wherein immediate attention to a change of such vital signals must be paid. The device comprises a programmable user interface 24-1 comprising a user interface item 25-1 for controlling, via a central processing unit, a connecting unit 21 to connect with a designated vital sign monitor 10 via status signal received therefrom. While the communication between the connection unit 21 and the monitors 10 may be two-directional, typically this communication is unidirectional in that the system unidirectional receives status signal data from the designated vital sign monitor 10. In connection therewith, a user interface item 25-2 may be provided for selecting a vital sign monitor signal of interest of a vital sign monitor 10 in communication with the vital sign monitor system, in case a monitor 10 forwards a plurality of monitor signals SSa,b, e.g. a datasignal SS-1$a$ representing a heart beat and a datasignal SS-1$b$ representing a respiratory rate. A suitable representation of such interface items are known and will not be further described.

In addition an activity monitor module 26 is provided. The activity module 26 may have a plurality of activity detector functions further exemplified in FIG. 2. In particular, module 26 is configured to register a mobile communication device's physical location of a designated professional and store it in a memory to update known location of a designated professional that is connected to the vital sign monitoring system 20. The activity monitor module 26 comprises a user interface item 27-1 for inputting a work activity from selected work activities. That is, for each designated professional a table is updated in memory of module 26 of past, current and future tasks with an execution status and a decision function to decide the progression of tasks. This update may be performed manually via item 27-1 or by coupling via that item 27-1 with programmed workflow routines that provide updates to the task stored in memory that may be in part automatic and in part manual.

The activity module 26 furthermore comprises a function to produce an availability indication based on the inputted work activity and physical locations, and forwards this to the central processing module 23.

Vital sign monitoring system 20 further comprises a communication module 22 under control of the processing module 23 arranged for connecting a plurality of mobile communication devices 30 . . . 30" of designated professionals in the intensive care unit. The communication unit 22 provides a suitable communication connection with communication devices 30, 30', via wireless internet or any suitable mobile phone signal connection. The communication module of the vital sign monitoring system can interface with existing (general purpose) communication networks (Wifi, internet, cellular, DECT), so that the system is not limited to communication handled exclusively by the vital sign monitoring system. Only one or even no professional may be connected to the vital signs monitoring system. E.g. when a neurosurgeon wants to call an intensivist for a specific patient, the intensivist may be connected to the vital sign monitoring system, but the neurosurgeon may not.

In the communication devices 30 . . . 30" a user interface item is provided for initiating communication. The user interface item is responsive to availability indications of a designated professional 30 as will be further illustrated in subsequent Figures. To this end activity monitoring module 26 comprises a follow up function arranged to monitor follow up of the user to the perceptive signal MS-2. The follow up function may be arranged to alert another designated user 30" listed as back up user in the activity monitor module 26 e.g., by a signal MS-3.

Figure 2:
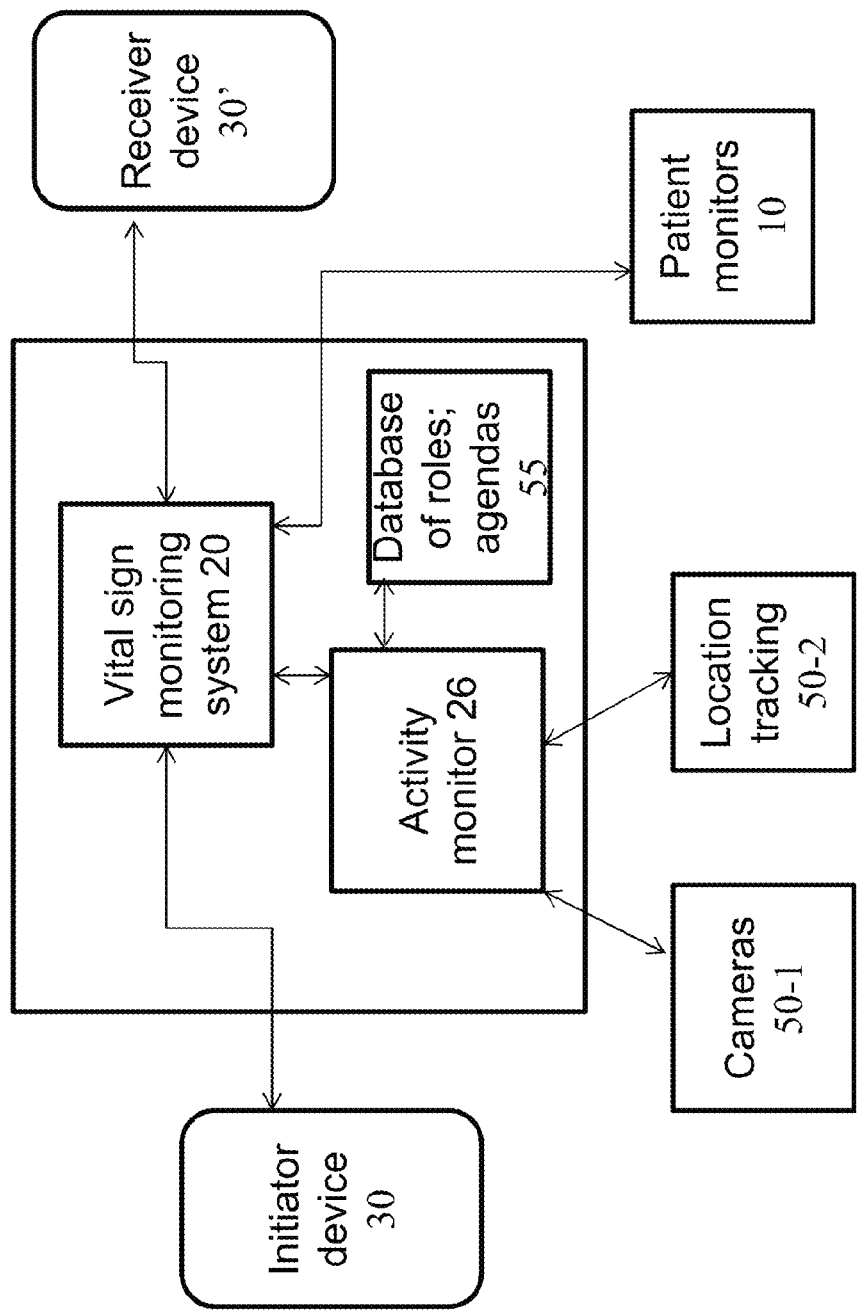
FIG. 2 shows the vital sign monitoring system in an exemplary context.

FIG. 2 shows a further schematic illustration of the activity module 26 and its constituting peripheral parts 50-1 . . . 2 functioning as activity detectors and updatable information storage items 55-1 . . . 2. Activity module 26 may provide context information from Cameras 50-1, Location tracking 50-2 devices; Agendas of staff 55-1, Database of roles and responsibilities of staff 55-2. The context information is used by the monitoring system 20 to determine a.o. the urgency of a call from patient monitors 10 and the availability of receivers devices 30'.

Table 1 details exemplary information provided to the initiator, including ways to detect that information

| Information for initiator | Achieved by |
| --- | --- |
| Who is responsible for the patient | Agenda and database of roles and responsibilities |
| Who to contact for role | Agenda and database of roles and responsibilities |
| Availability of receiver | Automatic activity detection, agenda and location detection |
| Location | Location tracking |
| Patient status | Vital signs |

Table 2 shows exemplary information that is provided to the receiver, including ways to detect that information

| Information for receiver | Achieved by |
| --- | --- |
| Who is the initiator? | Phone book |
| Role of the initiator | Agenda and database of roles and responsibilities |
| Responsibility for which patients? | Agenda and database of roles and responsibilities |
| Urgency of phone call | Manual, activity detection, patient status, location |
| Location of initiator | Location tracking |
| Patient status | Vital signs |

FIG. 3 shows in more detail the arrangement of the mobile communication device 30 embodied as a mobile phone. Suitable variants may be implemented in a pager or text messaging device. FIG. 3A shows user interface items on a screen of the mobile phone for initiating communication with another designated professional. In FIG. 3B user interface items are shown on a screen of a receiver for accepting communication. In FIG. 3A, in an on screen interface item, the availability of the user is shown. This information can be automatically detected and displayed using activity detection, location detection, and agenda. In another interface item search input can be entered to find an appropriate receiver for initiating communication with another designated professional connected to the vital sign monitoring system. For example, searching is possible based on professional role ("Intensivist"), on patient name ("Pietersen") or by specifying the Name of the person that needs to be called. In another interface item the search result shows a designated receiver, together with role, location and availability. In another user interface item for the initiator the urgency of the interruption is displayed based on the patient status, so that a communication urgency level is selected for another designated professional based on the vital sign indication. This can be adjusted manually. Finally, the initiator can select the type of communication.

FIG. 3B shows a screen for the receiver of the phone call. On the screen a user interface item is displayed for accepting communication with the professional seeking contact with an indicator of the selected urgency level based on the vital sign indication. An urgency level may be provided, by the communication function by a ringtone or notification that is automatically adjusted to the urgency of a message and to the availability of a receiver. For example, even when the receive may be busy—not-available—urgent messages can still be transferred by screen flashes indicating an urgent communication request. Also, a user interface item is displayed for showing availability indications of the designated professional. Here, the availability is automatically detected by GPS tracking or short range wireless tracking. Next, the initiator is listed with information about the role, responsible patients, location and urgency of the interruption. And finally, the options are given to deny or accept the phone call. Additionally, and option to forward a call to another caregiver can be added.

FIG. 4 shows in more detail the arrangement of the mobile communication device 30 embodied as a mobile phone. Suitable variants may be implemented in a pager or text messaging device. A communication function 31 is provided, e.g. a wifi or bluetooth module, or any other short range wireless communication device, for communicating with the vital sign monitoring system 20. A user interface item 35-1 is provided for initiating communication with another designated professional connected to the vital sign monitoring system. For this processing unit 33 communicates via the communicating function 31 with the monitoring system 20. User interface item 35-1 is arranged to select from this data communication MS a further designated professional based on a received availability level of the designated person. Another user interface item 35-2 is provided for accepting communication with a professional seeking contact with an indicator of the selected urgency level based on the vital sign indication.

While example embodiments were shown for systems and methods, also alternative ways may be envisaged by those skilled in the art having the benefit of the present disclosure for achieving a similar function and result. E.g. some components may be combined or split up into one or more alternative components. For example, while preferably, the same message transfer network is used for both receiving and sending of electronic messages, this may also be done via separate networks. Furthermore, while preferably the local data network is separate from the message transfer network, alternatively, the local data network and message transfer network may be part of an integrated network. Finally, the above-discussion is intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage.

The invention claimed is:

1. A method of connecting a mobile communication device to a communication module of a vital sign monitoring system arranged for connecting with a plurality of vital sign monitors for registering vital sign indications of specified nature and origin of respective patients and for connecting a plurality of mobile communication devices of designated professionals in an intensive care unit, comprising:
   in an initiation mode:
      selecting, by a communication function of the mobile communication device responsive to vital sign indications of specified nature and origin of a respective patient in the intensive care unit, a communication urgency level for another designated professional based on a vital sign indication from the vital sign monitoring system;
      receiving, at the mobile communication device, from the vital sign monitoring system, an identification of at least one other professional connectable to the vital sign monitoring system, based on an availability level of the at least one other professional; and
      initiating, by a user interface item in the mobile communication device, communication with an other communication device of a designated professional, wherein the user interface item is arranged to enable selection of the designated professional from among the at least one other professional; and
   in a reception mode:
      accepting, at the mobile communication device, communication from the vital sign monitoring system including an indicator of an urgency level set by an other mobile communication device based on the vital sign indication.

2. A non-transitory computer-readable medium that includes a computer program that, when executed by a processor, causes a mobile communication device to perform the method of claim 1.

3. A vital sign monitoring system comprising:
   an interface that receives one or more vital signs of a patient from one or more vital sign monitors;
   a central processing unit that determines that intervention may be required, based on the received vital signs; and
   if intervention may be required:
      establishes communications with a first communication device of a first medical professional;

communicates one or more of the vital signs of the patient to the first communication device;

receives, from the first communication device, a query regarding second professionals that should receive notification of the vital signs of the patient and an indication of an urgency level associated with the patient;

retrieves, from a database, an identification of one or more second medical professionals based on the query;

selects one or more available second medical professionals from among the identified one or more medical professionals, based on an availability of each of the identified one or more second medical professionals;

communicates the identification of the one or more selected available medical professionals to the first communication device;

receives, from the first communication device, a selection of a preferred second medical professional to receive the vital signs of the patient from among the one or more selected available medical professionals;

communicates, to a second communication device of the preferred second medical professional, an identification of the patient and the urgency level; and, receives, from the second communication device, a confirmation that the identification of the patient and the urgency level have been received by the second communication device.

4. The system of claim 3, comprising:

an activity monitor module that registers a mobile communication device's physical location of the one or more second medical professionals and receives a work activity from selected work activities; and an availability module that produces an availability indication based on the work activity and the physical location of each of the one or more second medical professionals;

wherein the central processing unit identifies the one or more selected available medical professionals based on the availability of each of the one or more second medical professionals.

5. The system of claim 3, wherein the confirmation from the second communication device includes an indication that the preferred second medical professional accepts or declines responsibility for the patient.

6. The system of claim 3, wherein the confirmation from the second communication device includes a request to forward the identification of the patient and the urgency level to a third professional.

7. The system of claim 3, wherein the central processing unit also communicates the vital signs to the second professional.

8. The system of claim 3, wherein the central processing unit also receives a selected availability level from the first professional, and selects the one or more available second medical professionals based on the selected availability level.

9. The system of claim 3, wherein the interface receives one or more further vital signs of the patient, and the central processing unit is configured to provide further communications with the first or second professional based on these further vital signs.

10. The system of claim 3, wherein the central processing unit communicates with a third professional if the first or second professional does not respond to the further communications.

11. The system of claim 3, wherein the central processing unit communicates the urgency level to the first or second professional by automatic adjustment of a ringtone, vibration intensity, or screen flash.

12. The system of claim 3, wherein the query identifies a role of the second professional.

13. The system of claim 3, wherein the query identifies a name of the second professional.

14. A mobile communication device comprising:

a communication interface element that:
    receives a first communication from a vital sign monitoring system that identifies one or more of the vital signs of a patient;

a processing element that presents an interface to a first medical professional and receives from the first medical professional a query related to second professionals that should receive notification of the vital signs of the patient and an identification of an urgency level associated with the patient;

wherein:

the communication interface element receives an identification of one or more available second medical professionals based on the query;

the interface receives from the first medical professional a selection of a preferred second medical professional from the one or more available second medical professionals to receive the vital signs of the patient; and the communication interface element communicates an identification of the preferred second medical professional to the vital sign monitoring system to effect communication of an identifier of the patient and the associated urgency level to the preferred second medical professional by the vital sign monitoring system.

15. The device of claim 14, wherein the query includes a selected availability level from the first medical professional, and the vital sign monitoring system uses the selected availability level to identify the one or more second medical professionals.

16. The device of claim 14, wherein the processing system notifies the first medical professional of the urgency by automatic adjustment of a ringtone, vibration intensity, or screen flash.

17. The device of claim 14, wherein the query identifies a role of the second professional.

18. The device of claim 14, wherein the query identifies a name of the second professional.

* * * * *